US010417793B2

(12) United States Patent
Chen

(10) Patent No.: US 10,417,793 B2
(45) Date of Patent: Sep. 17, 2019

(54) SYSTEM AND METHOD FOR DATA-CONSISTENCY PREPARATION AND IMAGE RECONSTRUCTION

(71) Applicant: Wisconsin Alumni Research Foundation, Madison, WI (US)

(72) Inventor: Guang-Hong Chen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 104 days.

(21) Appl. No.: 15/467,574

(22) Filed: Mar. 23, 2017

(65) Prior Publication Data

US 2018/0276852 A1 Sep. 27, 2018

(51) Int. Cl.
*G06T 11/00* (2006.01)
*G01R 33/565* (2006.01)
*G01N 23/046* (2018.01)

(52) U.S. Cl.
CPC .......... *G06T 11/003* (2013.01); *G01N 23/046* (2013.01); *G01R 33/565* (2013.01); *G01N 2223/401* (2013.01)

(58) Field of Classification Search
CPC ........ G06T 11/003; G06T 7/10; G06T 7/0012
See application file for complete search history.

(56) References Cited

U.S. PATENT DOCUMENTS

| 6,587,598 | B1* | 7/2003 | Devillers | A61B 6/5241 |
| | | | | 382/130 |
| 2007/0121779 | A1* | 5/2007 | Nishide | G06T 11/005 |
| | | | | 378/4 |
| 2011/0110572 | A1* | 5/2011 | Guehring | A61B 6/5258 |
| | | | | 382/131 |
| 2011/0282204 | A1* | 11/2011 | Shibata | A61B 8/06 |
| | | | | 600/443 |

(Continued)

FOREIGN PATENT DOCUMENTS

GB 1283915 8/1972

OTHER PUBLICATIONS

Li, Yingsheng, Garrett, John, Chen, Guang-Hong, Reduction of beam hardening artifacts in cone-beam CT imaging via SMART-RECON algorithm. Medical Imaging 2016: Physics of Medical Imaging, 97830W (Mar. 22, 2016). (Year: 2016).*

(Continued)

*Primary Examiner* — Kim Y Vu
*Assistant Examiner* — Molly Delaney
(74) *Attorney, Agent, or Firm* — Quarles & Brady LLP

(57) ABSTRACT

A system and method for reconstructing an image of a subject includes acquiring a reference dataset and reconstructing a prior image of the subject from the reference dataset and selecting at least a portion of the prior image that corresponds to a portion of the prior image of the subject that is free of artifacts. The method also includes acquiring a medical imaging dataset of the subject, performing a vertical (Continued)

comparison of the medical imaging dataset and the reference dataset to create a data inconsistency metric, and repeating the preceding steps to create a plurality of data inconsistency metrics. The method further includes performing a horizontal comparison of the data inconsistency metrics to identify inconsistent data, compensating for the inconsistent data, and reconstructing an image of the subject with reduced artifacts compared to the prior image.

21 Claims, 7 Drawing Sheets

(56) References Cited

U.S. PATENT DOCUMENTS

| | | | |
|---|---|---|---|
| 2014/0140601 A1* | 5/2014 | Litvin | G06T 11/005 382/131 |
| 2014/0270434 A1* | 9/2014 | Gulaka | G01R 33/543 382/128 |
| 2014/0270439 A1* | 9/2014 | Chen | G06T 11/006 382/131 |

OTHER PUBLICATIONS

Alvarez, et al., "Energy-selective reconstructions in x-ray computerised tomography," Physics in medicine and biology 21, 733 (1976).
Brooks, et al., "Beam hardening in x-ray reconstructive tomography," Physics in medicine and biology 21, 390 (1976).
Censor, et al., "A method of iterative data refinement and its applications," Mathematical methods in the applied sciences 7, 108-123 (1985).
Chen, et al., "A new data consistency condition for fan-beam projection data," Medical physics 32, 961-967 (2005).
Chen, et al., "Synchronized multiartifact reduction with tomographic reconstruction (SMART-RECON): A statistical model based iterative image reconstruction method to eliminate limited-view artifacts and to mitigate the temporal-average artifacts in time-resolved CT," Medical physics, vol. 42, No. 8, pp. 4698-4707, 2015.
Clackdoyle, et al., "Full data consistency conditions for cone-beam projections with sources on a plane," Physics in Medicine and Biology, vol. 58, No. 23, p. 8437, 2013.
De Man, et al., "An iterative maximum-likelihood polychromatic algorithm for CT," Medical Imaging, IEEE Transactions on 20, 999-1008 (2001).
Elbakri, et al., "Segmentation-free statistical image reconstruction for polyenergetic x-ray computed tomography with experimental validation," Physics in medicine and biology 48, 2453 (2003).
Gado, et al., "The peripheral zone of increased density in cranial computed tomography 1," Radiology 117, 71-74 (1975).
Hammersberg, et al., "Correction for beam hardening artefacts in computerised tomography," Journal of X-ray Science and Technology 8, 75-93 (1998).
Helgason, "Radon-fourier transforms on symmetric spaces and related group representations," Bull. Amer. Math. Soc., vol. 71, No. 5, pp. 757-763, Sep. 1965.
Herman, et al., "A comparative study of two postreconstruction beam hardening correction methods," Medical Imaging, IEEE Transactions on 2, 128-135 (1983).
Herman "Correction for beam hardening in computed tomography," Physics in medicine and biology 24, 81 (1979).
Herman, "Demonstration of beam hardening correction in computed tomography of the head," Journal of computer assisted tomography 3, 373-378 (1979).
Hsieh, et al., "An iterative approach to the beam hardening correction in cone beam CT," Medical physics 27, 23-29 (2000).
Jennings "A method for comparing beam-hardening filter materials for diagnostic radiology," Medical physics 15, 588-599 (1988).
John "The ultrahyperbolic differential equation with four independent variables," Duke Math. J., vol. 4, No. 2, pp. 300-322, Jun. 1938.
Joseph, et al., "A method for simultaneous correction of spectrum hardening artifacts in CT images containing both bone and iodine," Medical physics 24, 1629-1634 (1997).
Joseph, et al., "A method for correcting bone induced artifacts in computed tomography scanners," Journal of computer assisted tomography 2, 100-108 (1978).
Kachelriess, et al., "Empirical cupping correction: a first-order raw data precorrection for conebeam computed tomography," Medical physics 33, 1269-1274 (2006).
Kijewski, et al. "Correction for beam hardening in computed tomography," Medical physics 5, 209-214 (1978).
Kyriakou, et al., "Empirical beam hardening correction (EBHC) for CT," Medical physics 37, 5179-5187 (2010).
Ludwig "The radon transform on euclidean space," Communications on Pure and Applied Mathematics 19, 49-81 (1966).
McCullough, et al. "An Evaluation of the Quantitative and Radiation Features of a Scanning X-Ray Transverse Axial Tomograph: The EMI Scanner 1," Radiology 111, 709-715 (1974).
Meyer, et al., "Normalized metal artifact reduction (NMAR) in computed tomography," Medical physics, vol. 37, No. 10, pp. 5482-5493, 2010.
O'Sullivan, et al., "Alternating minimization algorithms for transmission tomography," Medical Imaging, IEEE Transactions on 26, 283-297 (2007).
Otsu "A threshold selection method from gray-level histograms," Automatica 11, 23-27 (1975).
Siewerdsen, et al., "Spektr: A computational tool for x-ray spectral analysis and imaging system optimization," Medical physics 31, 3057-3067 (2004).
Stonestrom, et al., "A framework for spectral artifact corrections in X-ray CT," IEEE Transactions on Biomedical Engineering 2, 128-141 (1981).
Yu, et al., "Data consistency based rigid motion artifact reduction in fan-beam ct," IEEE transactions on medical imaging 26, 249-260 (2007).
Yu, et al., "Dual-energy CT-based monochromatic imaging," American Journal of Roentgenology 680 199, S9-S15 (2012).

* cited by examiner

SYSTEM AND METHOD FOR DATA-CONSISTENCY PREPARATION AND IMAGE RECONSTRUCTION

STATEMENT REGARDING FEDERALLY SPONSORED RESEARCH

This invention was made with government support under EB021183 awarded by the National Institutes of Health. The government has certain rights in the invention.

BACKGROUND

The present disclosure relates to systems and methods for medical image data preparation and/or reconstruction. More particularly, systems and method are provided for processing medical imaging data to promote consistency and reconstruct images with controlled artifacts.

With conventional image reconstruction techniques, such as filtered backprojection for multi-detector CT (MDCT), C-arm cone beam CT (CBCT) imaging, CBCT for radiation therapy guidance, and Fourier-based reconstructions techniques for magnetic resonance imaging (MRI), a single image is reconstructed from a corresponding set of data acquired with the medical imaging system. For example, one image is reconstructed from a single sinogram in x-ray MDCT, CBCT imaging and one image is reconstructed from one k-space data set in MRI. This correspondence between data and the images reconstructed from that data is a function of traditional image reconstruction techniques and the fact that such techniques are based on an assumption that all of the acquired data are consistent with each other. Routinely, however, data acquired with medical imaging systems are not consistent with a single true image of the subject being imaged, or a single state of a true image object that has dynamic characteristics.

These inconsistencies manifest as artifacts in the reconstructed images and can have many different origins. For example, in x-ray MDCT and CBCT imaging, artifacts can result from the use of polychromatic x-ray spectrum in data acquisition, the presence of metal objects in the subject, by acquiring too few projections, from beam-hardening effects, from x-ray scatters, subject motion including cardiac motion, respiratory motion, and inadvertent body motion during data acquisitions, and so on. In MRI, artifacts can result from undersampling k-space, receiver coil sensitivity, magnetic field inhomogeneities, subject motion, and so on. Inconsistencies between the acquired data and the stationary state of a true image of the subject can also have other sources, such as the presence of an exogenous contrast agent that administered to the subject and the dynamic uptakes through the subject's vasculature. The assumption that the reconstructed image should be consistent with the acquired data is embodied in the following imaging model:

$$AI = Y \quad (1);$$

which states that image reconstruction techniques should seek to reconstruct an image, I, that when forward projected match with the acquired data, Y. The matrix, A, is referred to as the system matrix, which can be generally regarded as a forward projection operator that relates the reconstructed image, I, to the acquired data samples, Y. Eqn. (1) imposed that the reconstructed image, I, must be consistent with the measured data samples, Y; thus, Eqn. (1) can also be referred to as the "data consistency condition." In x-ray CT imaging, the system matrix can include a reprojection operation and in MRI the system matrix can include a Fourier transform operation. The consistency condition of Eqn. (1), put in other words, states that when an image is faithfully reconstructed, the forward projection of that image should be substantially similar to, or consistent with, the data actually acquired with the imaging system.

Additionally, to reconstruct an image, I, from the measured data, Y, it is often required that the data satisfy the so-called data sufficiency condition, which is a condition that allows for an inverse reconstruction formula to be used to reconstruct the image from the measured data. In x-ray CT imaging, the data sufficiency condition is the so-called Tuy condition, which requires the data samples to be acquired in an extended angular range around the image object. In MRI, the data sufficiency condition is the complete population of the entire Fourier space.

Even when the data sufficiency condition is satisfied, however, still another condition needs to be met to reconstruct a true image of the image object. The discretely acquired data samples also need to satisfy the associated sampling criterion for a given reconstruction scheme and be sufficiently consistent with itself. Examples of data sampling criteria include the view angle sampling requirement in x-ray CT and the Nyquist sampling criterion in MRI.

When the data sufficiency condition and data sampling criterion are met in x-ray CT, filtered backprojection can be used to reconstruct an image, and when both data sufficiency condition and data sampling criterion are met in MRI, Fourier inversion can be used to reconstruct an image.

When an iterative image reconstruction method is employed, the data sufficiency condition and data sampling criteria can be relaxed to some extent. One example of such a method is compressed sensing based iterative image reconstruction techniques.

In an ideal situation, when the aforementioned data sufficiency condition and data sampling conditions are satisfied, an artifact-free image can be reconstructed. This ideal situation is impractical in the real world, however, due to the non-ideal nature of all the hardware data acquisition systems and complications from the objects being imaged. As a result of these complications, the acquired data may not represent the same physical state of the image object, or may not be acquired under the same physical conditions. Thus, the acquired data are referred to as "inconsistent data." That is, such inconsistent data lacks consistency within and between the data, beyond any data sufficiency and sampling issues. The physical reasons for these inconsistencies, whether because of a non-ideal acquisition system or because of a change in the physical state of the object during data acquisition, are referred to as the sources of inconsistency.

When the acquired data are no longer consistent due to sources of inconsistency, such as those described above, the consistency condition begins to break down. That is, the acquired data are no longer consistent when physical effects such as subject motion, contrast enhancement, noise, beam hardening in x-ray imaging, and so on are present during the data acquisition process. The inconsistencies in the acquired data manifest as artifacts in the reconstructed images.

Although a qualitative correlation between data inconsistency and the resultant image artifacts is known, there are no widely-accepted, systematic ways to quantify the relationship between artifacts and data inconsistency levels, or to develop image reconstruction algorithms that incorporate data consistency evaluation and classification into reconstruction process to sufficiently mitigate image artifacts caused by the many different types and causes of data inconsistency. At best, in the case of CT imaging, some have provided mathematical data consistency conditions for the entire set of line integrals of attenuation coefficients for parallel-beam line integrals and divergent fan-beam line integrals, and these conditions have been utilized as guiding principle to either complete the missing line integrals or to compensate for object movement during the data acquisition process. These characterizations of data consistency are referred to as global characterizations since they do not tell whether one specific datum is consistent with others, or one view of data is consistent with data acquired at other view angles.

Thus, a need persists to invent new methods that are able to characterize intrinsic data consistency level from one datum to another or from one view of data to another view of data and to incorporate the new data consistency classification method into image reconstruction to produce medical and other images that are free from or otherwise not corrupted by artifacts, despite inconsistent data and/or undersampled data.

SUMMARY

The present disclosure overcomes the aforementioned drawbacks by recognizing that images without artifacts come from consistent data. Thus, systems and methods for analyzing imaging data are provided to create subsets of data with high level of data consistency to guide image reconstruction. These subsets of data can then be reconstructed into images with substantially reduced image artifacts. In one example, reconstruction may be performed using a reconstruction technique that jointly reconstructs all sub-image volumes, each volume corresponds to one subset of data with designated consistency level, such as SMART-RECON.

In accordance with one aspect of the disclosure, a method for reconstructing an image of a subject is provided that includes a) acquiring a data set that meets the sufficiency condition and reconstructing an image of the subject and b) segmenting or filtering the reconstructed image to generate a prior image of the subject that is free of artifacts. The method also includes c) generating synthetic projection data using the the prior image, d) performing a vertical comparison of the synthetic projection data and the physically measured data to create a data inconsistency metric, and e) repeating the step d) over the entire acquired data set to create a quantification of data data inconsistency level for each acquired view angles. The method further includes f) performing a horizontal comparison of the data inconsistency metrics among the acquired view angles to identify inconsistent data, g) compensating for the inconsistent data identified in step f), and h) reconstructing an image of the subject with reduced artifacts compared to the prior image.

In accordance with another aspect of the disclosure, a method for reconstructing an image of a subject includes a) generating synthetic image data using at least a portion of prior image data acquired from a subject and b) calculating a plurality of data inconsistency metrics by comparing the synthetic image data and medical imaging data. The method also includes c) dividing the plurality of data inconsistency metrics into classes based on predetermined data inconsistency metric steps and d) initializing an image matrix having columns that each correspond to data in each of the classes. The method further includes e) reconstructing a plurality of images of the subject by i) minimizing a matrix rank of the image matrix and ii) constraining the rank minimization of step e)i) subject to a consistency condition that promotes a forward projection of each column in the image matrix to be consistent with a column in the image matrix.

In accordance with yet another aspect of the disclosure, a computed tomography (CT) system includes an x-ray source and associated detectors configured to acquire imaging data from a subject over a range of view angles. The CT system also includes a computer system including a processor configured to a) control the x-ray source and associated detectors to acquire imaging data from the subject, b) reconstruct the imaging data into a prior image of the subject, and c) segment the prior image to create segmented imaging data that is substantially free of artifacts. The computer system is further programmed to d) generate synthetic image data using the segmented imaging data, e) calculate a plurality of data inconsistency metrics by comparing the synthetic image data and the segmented imaging data, and f) divide the plurality of data inconsistency metrics into classes based on data inconsistency metric steps. The computer system is also programmed to g) initialize an image matrix having columns that each correspond to data in each of the classes and h) reconstruct a plurality of images of the subject by i) minimizing a matrix rank of the image matrix and ii) constraining the rank minimization of step h)i) subject to a consistency condition that promotes a forward projection of each column in the image matrix to be consistent with a column in the image matrix.

In accordance with still another aspect of the disclosure, a method is provided for generating tomographic images. The method includes a) acquiring a tomographic dataset of a subject, b) reconstructing the initial image from the tomographic dataset, and c) generating a prior image of the subject that is free of artifacts from at least one of the tomographic dataset or initial image. The method also includes d) generating a synthetic reference dataset from the prior image, e) performing a vertical comparison of the synthetic reference dataset and the tomographic dataset to create a plurality of data inconsistency metrics, and f) performing a horizontal comparison of data inconsistency level across the plurality of data inconsistency metrics. The method also includes g) sorting the tomographic dataset into data consistency classes using the data inconsistency metrics, h) selectively reconstructing a least one image from portions of the tomographic dataset determined to be consistent based on the data consistency classes, and i) selectively displaying the at least one image reconstructed at step h).

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1A:
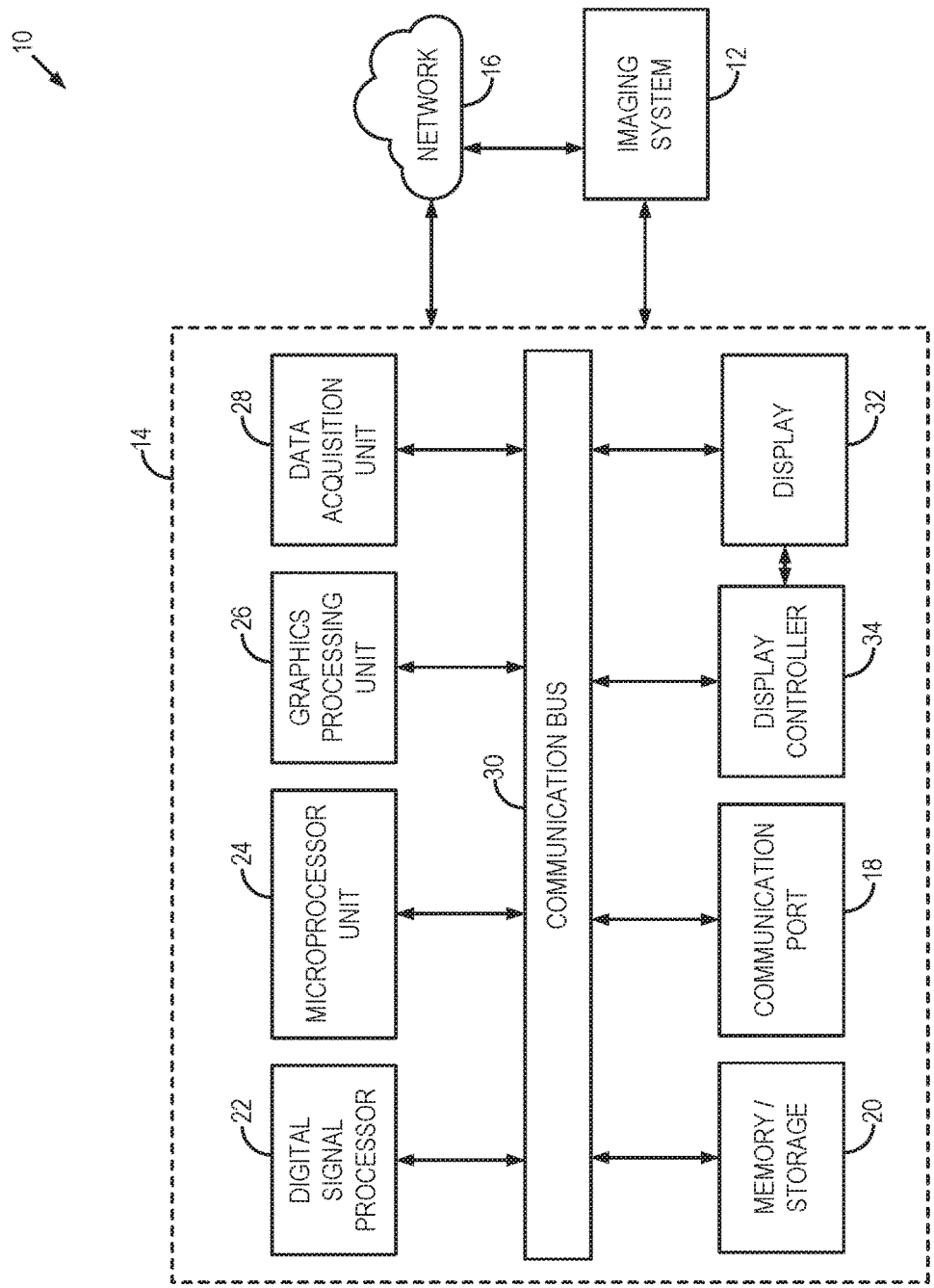
FIG. 1A is a schematic diagram of an example computer system that can be configured to implement the methods described herein.
Figure 1B:
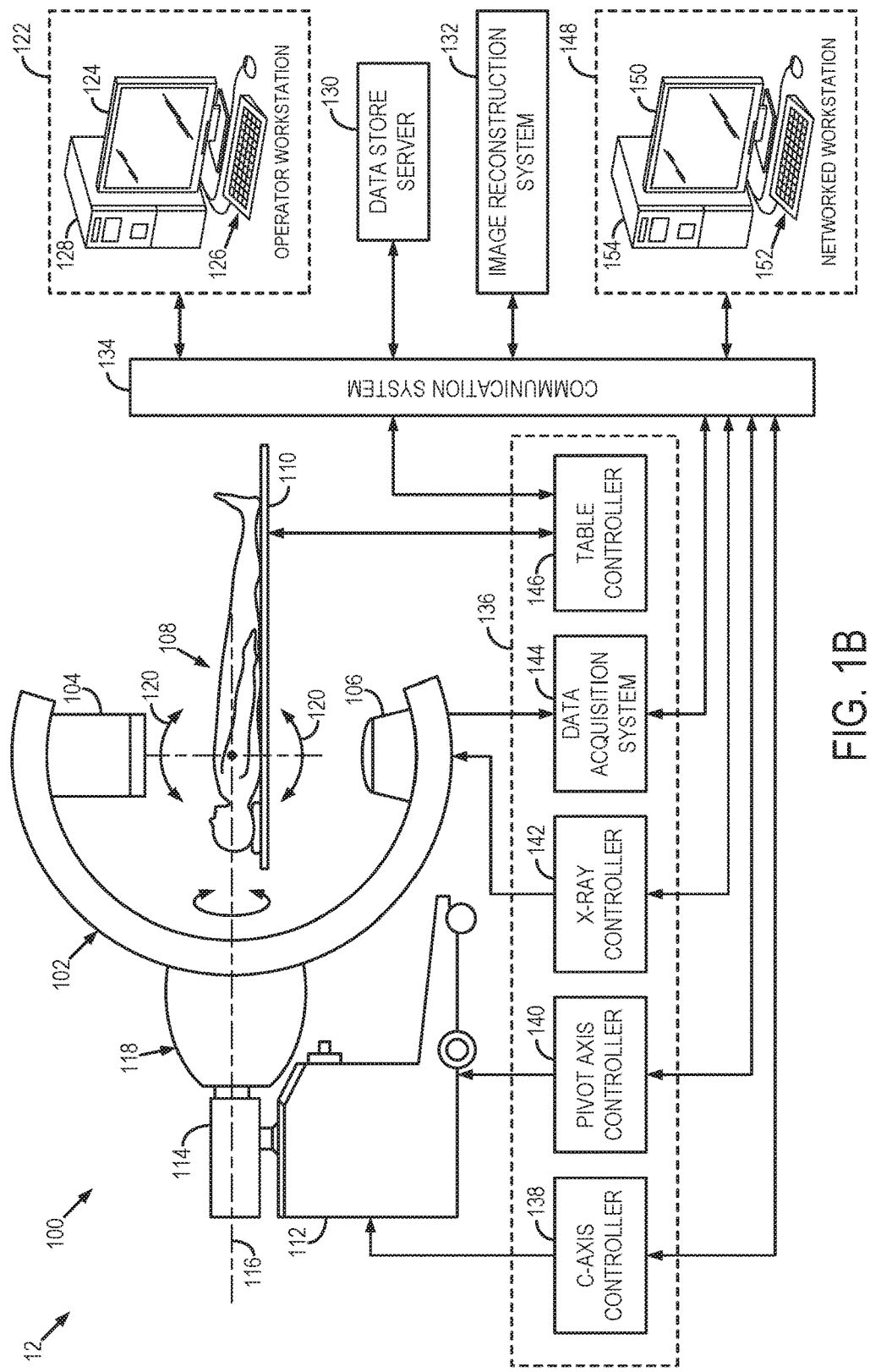
FIG. 1B is a schematic diagram of a C-arm x-ray computed tomography (CT) imaging system configured in accordance with the present disclosure.

Referring now to FIG. 1A, a block diagram of an example system 10 is provided that can be configured to carry out techniques, methods, and processes accordance with the present disclosure. The system may include an imaging system 12 that is coupled to a computer system 14. The coupling of the imaging system 12 to the computer system 14 may be a direct or dedicated network connection, or may be through a broad network 16, such as an intranet or the Internet.

The computer system 14 may be a workstation integrated with or separate from the medical imaging systems 12 or a variety of other medical imaging systems, including, as non-limiting examples, computed tomography (CT) system, magnetic resonance imaging (MRI) systems, positron emission tomography (PET) systems, single photon emission computed tomography (SPECT) systems, and the like. Furthermore, the computer system 14 may be a workstation integrated within the medical imaging system 12 or may be a separate workstation or mobile device or computing system. To this end, the following description of particular hardware and configurations of the hardware of the example computer system 14 is for illustrative purposes. Some computer systems may have varied, combined, or different hardware configurations.

Medical imaging data acquired by the medical imaging system 12 or other imaging system can be provided to the computer system 14, such as over the network 16 or from a storage device. To this end, the computer system 14 may include a communications port or other input port 18 for communication with the network 16 and system coupled thereto. Also, the computer system 14 may include memory and storage capacity 20 to store and access data or images.

In some configuration, computer system 14 may include one or more processing systems or subsystems. That is, the computer system 14 may include one or more physical or virtual processors. As an example, the computer system 14 may include one or more of a digital signal processor (DSP) 22, a microprocessor unit (MPU) 24, and a graphics processing unit (GPU) 26. If the computer system 14 is integrated into the medical imaging system, a data acquisition unit 28 may be connected directly to the above-described processor(s) 22, 24, 26 over a communications bus 30, instead of communicating acquired data or images via the network 16. As an example, the communication bus 30 can be a group of wires, or a hardwire used for switching data between the peripherals or between any component, such as the communication buses described above.

The computer system 14 may also include or be connected to a display 32. To this end, the computer system 14 may include a display controller 34. The display 32 may be a monitor connected to the computer system 14 or maybe integrated with the computer system 14, such as in portable computers or mobile devices.

Figure 2:
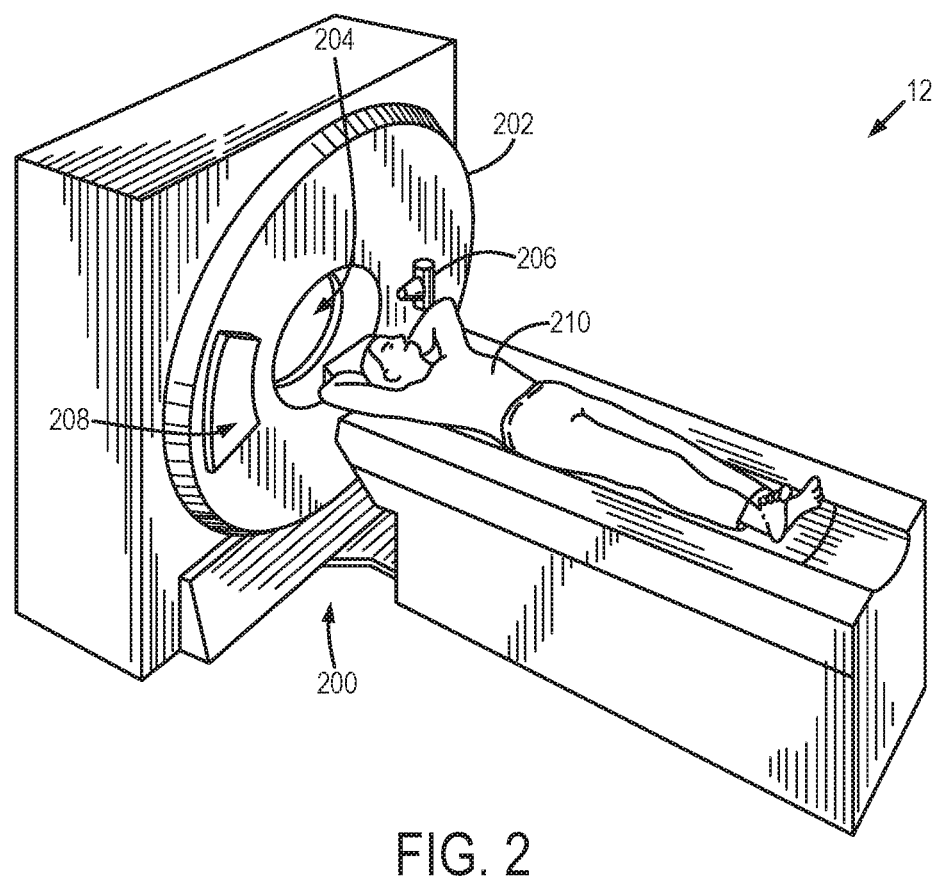
FIG. 2 is a perspective view of an example of an x-ray computed tomography (CT) system.

Referring to FIG. 1A, one, non-limiting example of the imaging system 12 is provided. Specifically, in this example, a so-called "C-arm" x-ray imaging system 100 is illustrated for use in accordance with some aspects of the present disclosure. Such an imaging system is generally designed for use in connection with interventional procedures. Such systems stand in contrast to, for example, traditional computed tomography (CT) systems 200, such as illustrated in FIG. 2. That is, the traditional CT system includes a gantry 202 that forms a bore 204 extending therethrough. In particular, the gantry 202 has an x-ray source 206 mounted thereon that projects a fan-beam, or cone-beam, of x-rays toward a detector array 208 mounted on the opposite side of the bore 204 through the gantry 202. Thus, when a subject 210 is arranged in the bore 204 for imaging using the source 206 and detector array 208, access to the subject 210 is restricted by the gantry 202.

Referring again to FIG. 1A, the C-arm x-ray imaging system 100 includes a gantry 102 having a C-arm to which an x-ray source assembly 104 is coupled on one end and an x-ray detector array assembly 106 is coupled at its other end. The gantry 102 enables the x-ray source assembly 104 and detector array assembly 106 to be oriented in different positions and angles around a subject 108, such as a medical patient or an object undergoing examination, which is positioned on a table 110. When the subject 108 is a medical patient, this configuration enables a physician access to the subject 108.

The x-ray source assembly 104 includes at least one x-ray source that projects an x-ray beam, which may be a fan-beam or cone-beam of x-rays, towards the x-ray detector array assembly 106 on the opposite side of the gantry 102. The x-ray detector array assembly 106 includes at least one x-ray detector, which may include a number of x-ray detector elements. Examples of x-ray detectors that may be included in the x-ray detector array assembly 106 include flat panel detectors, such as so-called "small flat panel" detectors. Such a detector panel allows the coverage of a field-of-view of approximately twelve centimeters.

Together, the x-ray detector elements in the one or more x-ray detectors housed in the x-ray detector array assembly 106 sense the projected x-rays that pass through a subject 108. Each x-ray detector element produces an electrical signal that may represent the intensity of an impinging x-ray beam and, thus, the attenuation of the x-ray beam as it passes through the subject 108. In some configurations, each x-ray detector element is capable of counting the number of x-ray photons that impinge upon the detector. During a scan to acquire x-ray projection data, the gantry 102 and the components mounted thereon rotate about an isocenter of the C-arm x-ray imaging system 100.

The gantry 102 includes a support base 112. A support arm 114 is rotatably fastened to the support base 112 for rotation about a horizontal pivot axis 116. The pivot axis 116 is aligned with the centerline of the table 110 and the support arm 114 extends radially outward from the pivot axis 116 to support a C-arm drive assembly 118 on its outer end. The C-arm gantry 102 is slidably fastened to the drive assembly 118 and is coupled to a drive motor (not shown) that slides the C-arm gantry 102 to revolve it about a C-axis, as indicated by arrows 120. The pivot axis 116 and C-axis are orthogonal and intersect each other at the isocenter of the C-arm x-ray imaging system 100, which is indicated by the black circle and is located above the table 110.

The x-ray source assembly 104 and x-ray detector array assembly 106 extend radially inward to the pivot axis 116 such that the center ray of this x-ray beam passes through the system isocenter. The center ray of the x-ray beam can thus be rotated about the system isocenter around either the pivot axis 116, the C-axis, or both during the acquisition of x-ray attenuation data from a subject 108 placed on the table 110.

During a scan, the x-ray source and detector array are rotated about the system isocenter to acquire x-ray attenuation projection data from different angles. By way of example, the detector array is able to acquire thirty projections, or views, per second.

The C-arm x-ray imaging system 100 also includes an operator workstation 122, which typically includes a display 124; one or more input devices 126, such as a keyboard and mouse; and a computer processor 128. The computer processor 128 may include a commercially available programmable machine running a commercially available operating system. The operator workstation 122 provides the operator interface that enables scanning control parameters to be entered into the C-arm x-ray imaging system 100. In general, the operator workstation 122 is in communication with a data store server 130 and an image reconstruction system 132. By way of example, the operator workstation 122, data store sever 130, and image reconstruction system 132 may be connected via a communication system 134, which may include any suitable network connection, whether wired, wireless, or a combination of both. As an example, the communication system 134 may include both proprietary or dedicated networks, as well as open networks, such as the internet.

The operator workstation 122 is also in communication with a control system 136 that controls operation of the C-arm x-ray imaging system 100. The control system 136 generally includes a C-axis controller 138, a pivot axis controller 140, an x-ray controller 142, a data acquisition system ("DAS") 144, and a table controller 146. The x-ray controller 142 provides power and timing signals to the x-ray source assembly 104, and the table controller 146 is operable to move the table 110 to different positions and orientations within the C-arm x-ray imaging system 100.

The rotation of the gantry 102 to which the x-ray source assembly 104 and the x-ray detector array assembly 106 are coupled is controlled by the C-axis controller 138 and the pivot axis controller 140, which respectively control the rotation of the gantry 102 about the C-axis and the pivot axis 116. In response to motion commands from the operator workstation 122, the C-axis controller 138 and the pivot axis controller 140 provide power to motors in the C-arm x-ray imaging system 100 that produce the rotations about the C-axis and the pivot axis 116, respectively. For example, a program executed by the operator workstation 122 generates motion commands to the C-axis controller 138 and pivot axis controller 140 to move the gantry 102, and thereby the x-ray source assembly 104 and x-ray detector array assembly 106, in a prescribed scan path.

The DAS 144 samples data from the one or more x-ray detectors in the x-ray detector array assembly 106 and converts the data to digital signals for subsequent processing. For instance, digitized x-ray data is communicated from the DAS 144 to the data store server 130. The image reconstruction system 132 then retrieves the x-ray data from the data store server 130 and reconstructs an image therefrom. The image reconstruction system 130 may include a commercially available computer processor, or may be a highly parallel computer architecture, such as a system that includes multiple-core processors and massively parallel, high-density computing devices. Optionally, image reconstruction can also be performed on the processor 128 in the operator workstation 122. Reconstructed images can then be communicated back to the data store server 130 for storage or to the operator workstation 122 to be displayed to the operator or clinician.

The C-arm x-ray imaging system 100 may also include one or more networked workstations 148. By way of example, a networked workstation 148 may include a display 150; one or more input devices 152, such as a keyboard and mouse; and a processor 154. The networked workstation 148 may be located within the same facility as the operator workstation 122, or in a different facility, such as a different healthcare institution or clinic.

The networked workstation 148, whether within the same facility or in a different facility as the operator workstation 122, may gain remote access to the data store server 130, the image reconstruction system 132, or both via the communication system 134. Accordingly, multiple networked workstations 148 may have access to the data store server 130, the image reconstruction system 132, or both. In this manner, x-ray data, reconstructed images, or other data may be exchanged between the data store server 130, the image reconstruction system 132, and the networked workstations 148, such that the data or images may be remotely processed by the networked workstation 148. This data may be exchanged in any suitable format, such as in accordance with the transmission control protocol ("TCP"), the Internet protocol ("IP"), or other known or suitable protocols.

Figure 3:
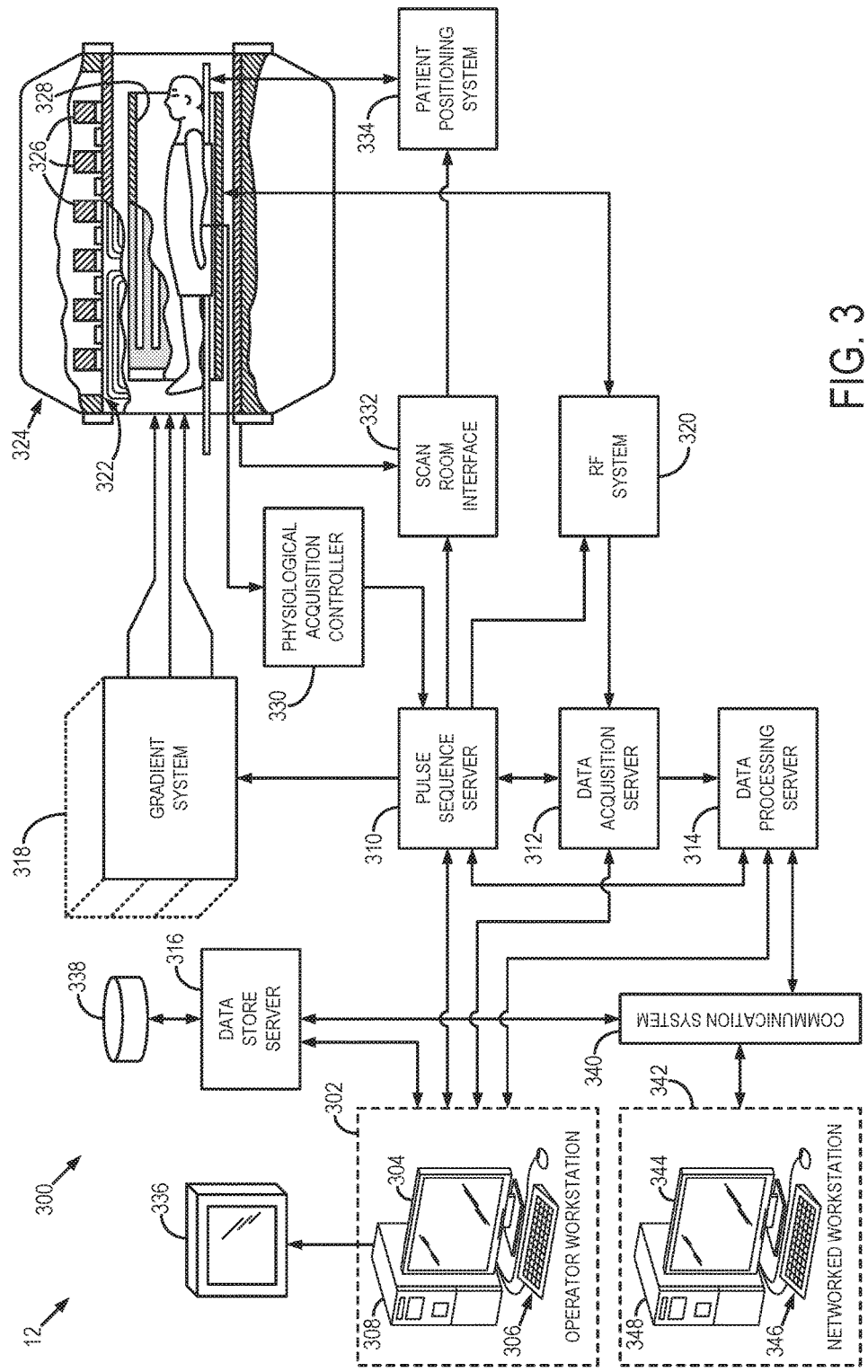
FIG. 3 is a block diagram of an example magnetic resonance imaging ("MRI") system that can implement methods described here.

Referring particularly now to FIG. 3, an example of a magnetic resonance imaging ("MR") or nuclear magnetic resonance (NMR) system 300 that can implement the methods described here is illustrated. The MR system 300 includes an operator workstation 302 that may include a display 304, one or more input devices 306 (e.g., a keyboard, a mouse), and a processor 308. The processor 308 may include a commercially available programmable machine running a commercially available operating system. The operator workstation 302 provides an operator interface that facilitates entering scan parameters into the MR system 300. The operator workstation 302 may be coupled to different servers, including, for example, a pulse sequence server 310, a data acquisition server 312, a data processing server 314, and a data store server 316. The operator workstation 302 and the servers 310, 312, 314, and 316 may be connected via a communication system 340, which may include wired or wireless network connections.

The pulse sequence server 310 functions in response to instructions provided by the operator workstation 302 to operate a gradient system 318 and a radiofrequency ("RF") system 320. Gradient waveforms for performing a prescribed scan are produced and applied to the gradient system 318, which then excites gradient coils in an assembly 322 to produce the magnetic field gradients $G_x$, $G_y$, and $G_z$ that are used for spatially encoding magnetic resonance signals. The gradient coil assembly 322 forms part of a magnet assembly 324 that includes a polarizing magnet 326 and a whole-body RF coil 328.

RF waveforms are applied by the RF system 320 to the RF coil 328, or a separate local coil to perform the prescribed magnetic resonance pulse sequence. Responsive magnetic resonance signals detected by the RF coil 328, or a separate local coil, are received by the RF system 320. The responsive magnetic resonance signals may be amplified, demodulated, filtered, and digitized under direction of commands produced by the pulse sequence server 310. The RF system 320 includes an RF transmitter for producing a wide variety of RF pulses used in MR pulse sequences. The RF transmitter is responsive to the prescribed scan and direction from the pulse sequence server 310 to produce RF pulses of the desired frequency, phase, and pulse amplitude waveform. The generated RF pulses may be applied to the whole-body RF coil 328 or to one or more local coils or coil arrays.

The RF system 320 also includes one or more RF receiver channels. An RF receiver channel includes an RF preamplifier that amplifies the magnetic resonance signal received by the coil 328 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2} \qquad (2);$$

and the phase of the received magnetic resonance signal may also be determined according to the following relationship:

$$\varphi = \tan^{-1}\left(\frac{Q}{I}\right). \qquad (3)$$

The pulse sequence server 310 may receive patient data from a physiological acquisition controller 330. By way of example, the physiological acquisition controller 330 may receive signals from a number of different sensors connected to the patient, including electrocardiograph ("ECG") signals from electrodes, or respiratory signals from a respiratory bellows or other respiratory monitoring devices. These signals may be used by the pulse sequence server 310 to synchronize, or "gate," the performance of the scan with the subject's heart beat or respiration.

The pulse sequence server 310 may also connect to a scan room interface circuit 332 that receives signals from various sensors associated with the condition of the patient and the magnet system. Through the scan room interface circuit 332, a patient positioning system 334 can receive commands to move the patient to desired positions during the scan.

The digitized magnetic resonance signal samples produced by the RF system 320 are received by the data acquisition server 312. The data acquisition server 312 operates in response to instructions downloaded from the operator workstation 302 to receive the real-time magnetic resonance data and provide buffer storage, so that data is not lost by data overrun. In some scans, the data acquisition server 312 passes the acquired magnetic resonance data to the data processor server 314. In scans that require information derived from acquired magnetic resonance data to control the further performance of the scan, the data acquisition server 312 may be programmed to produce such information and convey it to the pulse sequence server 310. For example, during pre-scans, magnetic resonance data may be acquired and used to calibrate the pulse sequence performed by the pulse sequence server 310. As another example, navigator signals may be acquired and used to adjust the operating parameters of the RF system 320 or the gradient system 318, or to control the view order in which k-space is sampled. In still another example, the data acquisition server 312 may also process magnetic resonance signals used to detect the arrival of a contrast agent in a magnetic resonance angiography ("MRA") scan. For example, the data acquisition server 312 may acquire magnetic resonance data and processes it in real-time to produce information that is used to control the scan.

The data processing server 314 receives magnetic resonance data from the data acquisition server 312 and processes the magnetic resonance data in accordance with instructions provided by the operator workstation 302. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 314 are conveyed back to the operator workstation 302 for storage. Real-time images may be stored in a data base memory cache, from which they may be output to operator display 302 or a display 336. Batch mode images or selected real time images may be stored in a host database on disc storage 338. When such images have been reconstructed and transferred to storage, the data processing server 314 may notify the data store server 316 on the operator workstation 302. The operator workstation 302 may be used by an operator to archive the images, produce films, or send the images via a network to other facilities.

The MR system 300 may also include one or more networked workstations 342. For example, a networked workstation 342 may include a display 344, one or more input devices 346 (e.g., a keyboard, a mouse), and a processor 348. The networked workstation 342 may be located within the same facility as the operator workstation 302, or in a different facility, such as a different healthcare institution or clinic.

The networked workstation 342 may gain remote access to the data processing server 314 or data store server 316 via the communication system 340. Accordingly, multiple networked workstations 342 may have access to the data processing server 314 and the data store server 316. In this manner, magnetic resonance data, reconstructed images, or other data may be exchanged between the data processing server 314 or the data store server 316 and the networked workstations 342, such that the data or images may be remotely processed by a networked workstation 342.

Motivated by the attempt to improve temporal resolution of C-arm cone beam CT dynamic imaging, a new iterative image reconstruction method, which was referred to as SMART-RECON, was developed to simultaneously reduce limited-view artifacts and temporal-average artifacts by a joint reconstruction of multiple images from a single short-scan CT data set. For example, systems and methods that implement and utilize the SMART-RECON techniques are described in U.S. Pat. No. 9,384,566 and co-pending U.S. application Ser. No. 15/211,448, both of which are incorporated herein by reference in their entirety. As described therein, each one of the jointly reconstructed images is consistent with the data acquired from a smaller view angle subset to reduce temporal average artifacts or equivalently to improve temporal resolution in contrast enhanced cone beam CT imaging.

The present disclosure recognizes that data that is not consistent (i.e., inconsistent data) yields images with artifacts. This premise, as described above, is understood. However, the present disclosure also recognizes that images that lack artifacts correspond to data that is consistent. Thus, as will be described, systems and methods are provided to assemble data into datasets using images or a modified version of images (prior images) that are free of artifacts. Furthermore, the present disclosure recognizes that SMART-RECON or other reconstruction techniques may be leveraged to reconstruct the assembled datasets in a way that mitigates artifacts due to inconsistent data.

More particularly, the present disclosure provides a practical means to define a data inconsistency metric (DIM) that can be used to locally characterize the inconsistency level of each acquired datum or a view of acquired data and systems and methods to use the DIM in a data classification technique to select an optimal data set with minimal data inconsistency level to reconstruct image with minimal artifacts contamination. As will be described the acquired datasets can be classified into one or more subsets based upon the value of DIM. After data classification, the SMART-RECON algorithm or other reconstruction technique can be applied to reconstruct these sub-images. Each sub-image is consistent with the subset of the projection view angles for a given range of DIM values. As a result, substantially improved images are provided.

As one non-limiting example of an application of this technique, the DIM can be used to quantify the level of spectral inconsistency of acquired data at each view angle in CT imaging. With this, the relationship between the level of data inconsistency and the severity of image artifacts can be systematically understood and leveraged to improve images. That is, according to the level of inconsistency, data can be sorted into different consistency classes for reconstruction, such as using SMART-RECON. Since each image corresponding to spectrally consistent data, spectral-inconsistency artifacts are less severe in each individual image. Additionally, since different consistency classes represent different spectral information of the same image object, attenuation coefficients of same type of tissue among these images could be different. As but one example, spectral-resolved imaging from a single short-scan data acquisition may be achieved via the proposed reconstruction method.

Figure 4A:
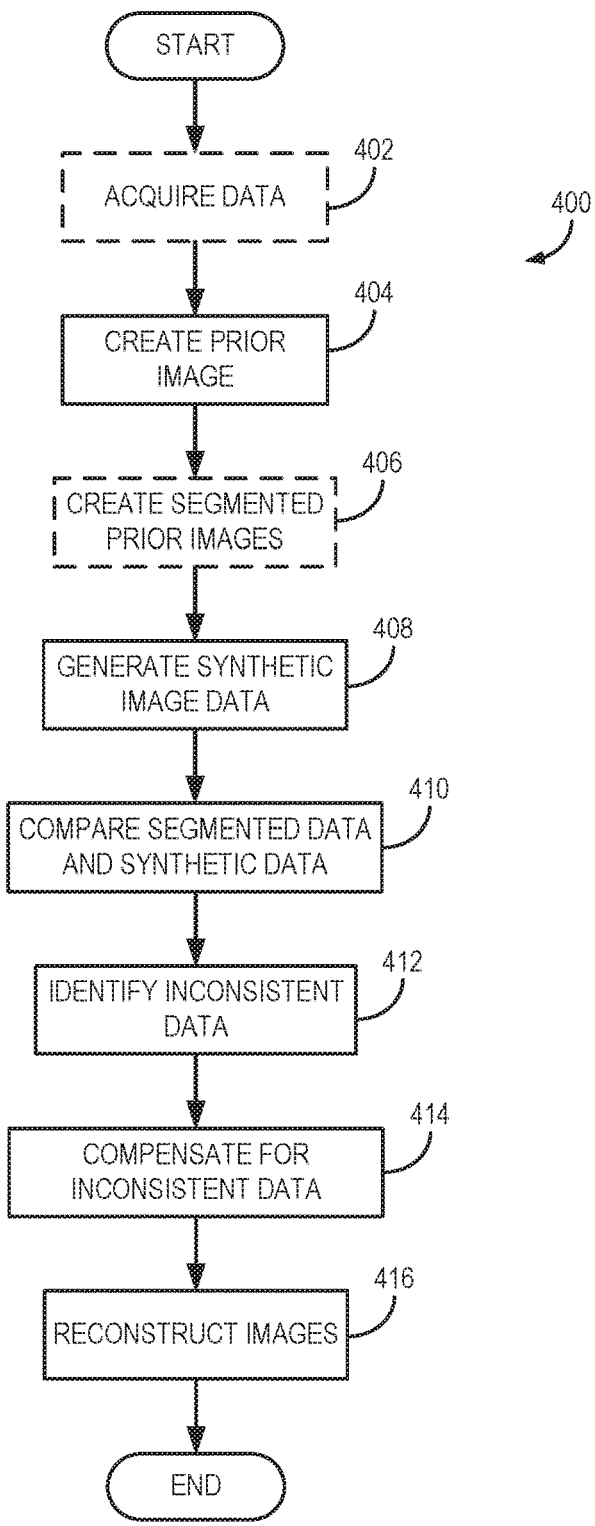
FIG. 4A is a flow chart setting forth non-limiting example steps of a method in accordance with the present disclosure.

Referring to FIG. 4A, one example of a process 400 for acquiring and reconstructing images in accordance with the present disclosure is provided. The process begins at process block 402 with the acquisition of imaging data. In this context, the acquisition of imaging data at process block 402 may include acquiring imaging data from a subject using an imaging system, including tomographic imaging systems such as CT, PET, SPECT, and others, as well as non-tomographic imaging systems, such as MRI systems. Also, the acquisition of imaging data at process block 402 may include acquiring or accessing stored imaging data that was previously acquired from a subject using an imaging system. The subject and, thus, the imaging data may be medical in nature or non-medical in nature. That is, the subject may be a person, animal, or other subject from which medical information may be derived. Also, the subject may include inanimate objects.

Again, the present disclosure also recognizes that images that lack artifacts correspond to data that is consistent. With this realization in place, the process 400 continues by creating a "prior image" at process block 404. The prior image may be reconstructed from the data acquired at process block 402 or, process block 402 may be optionally foregone, for example, if a suitable prior image is available, such as from a storage device holding previously-reconstructed images. As will be described, data sorting or classification can be used to improve consistency of data. In this case, data sorting can be used on the data reconstructed to form the prior image or the prior image can be created without data sorting. In either case, the prior image is created or selected to accurately represent the desired structures of the subject. In a medical image, the prior image is created or selected to accurately reflect the morphology and anatomical structure of the patient. In applications where the spectral information is of substantial importance, the prior image preferably does not contain any spectral-inconsistency artifacts. However, if basic anatomical images or spectral information is the priority, the prior image may then deviate from the true image object in terms of spatial resolution, temporal resolution, contrast resolution, or spectral resolution. That is, the prior image may include some artifacts.

At process block 406, the prior image is then segmented to generate a segmented prior image, $X_p$, that is without or is generally without artifacts germane to the purpose of the images being acquired. If the prior image at process block 404 is generally free of artifacts, process block 406 may be foregone. However, as explained above, medical imaging data typically includes some artifacts. Thus, at process block 406, the prior image from process block 404 is segmented into several classes (such as based on tissue or material classifications) such that artifacts within the segmented prior images are controlled.

At process block 408, synthetic image data is generated using the segmented prior images from process block 406 or the prior image from process block 404. For example, in the case of projection data (such as PET, CT, or projection-sampling of k-space for MR data) a forward projection is performed to generate the synthetic image data at each corresponding projection. If the MR data or other data is not composed from projections, a model may be used to construct synthetic data.

As but one non-limiting example, in the case of CT data, the forward projection is performed to generate synthetic image data at each view angle. Thus, the synthetic image data has one-to-one view angle correspondence with the projection data of the data acquired at process block 402. Thus, in this non-limiting example, this synthetic image data of the segmented prior image is consistent because it may be maintained to be, for example, temporally consistent and spatially consistent.

Figure 5:
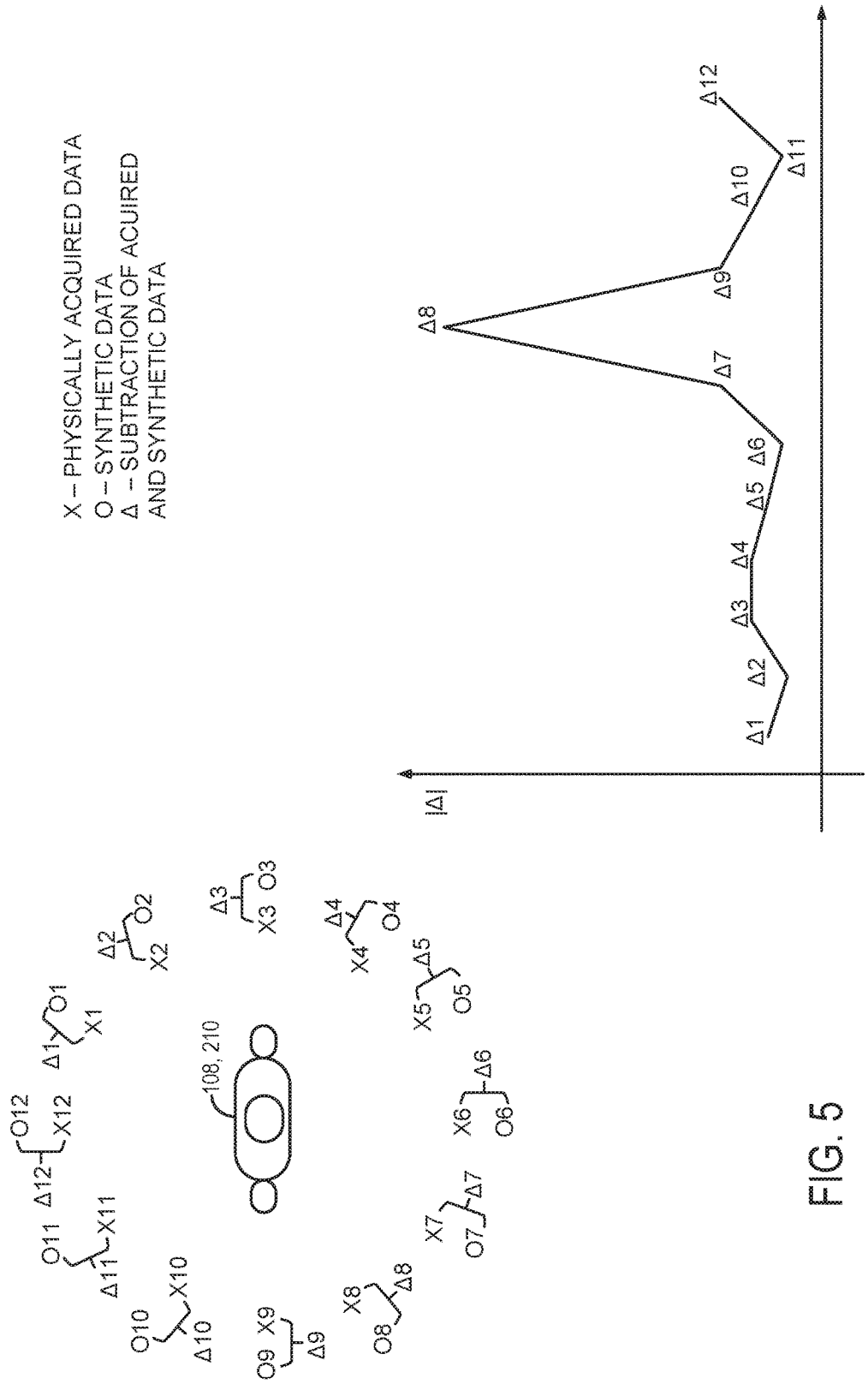
FIG. 5 is a pictorial illustrating data processing techniques in accordance with the present disclosure.

For example, referring to FIG. 5, a pictorial representation of the datasets and processing is provided. In FIG. 5, the subject 108, 210 described above is shown surrounded by the segmented projection data. Specifically, as described above the acquired projection data is segmented and, in this non-limiting example, the data has been segmented into 12 datasets X1-X12 that correspond to the segmented images. Thus, datasets X1-X12 represent physically acquired data arranged proximate to a position of the x-ray source when the projection was acquired. For example, projection data X12 is data acquired by the CT system when the x-ray source is generally positioned above the subject 108, 210 to acquire data using x-rays that pass from anterior to posterior. As also described above, each physically acquired dataset is forward projected or otherwise modeled to create a synthetic dataset O1-O12.

Notably, this example, for illustration purposes only, indicates that data segmentation is based heavily on projection angle. This is not necessarily the case and data segmentation should not be understood to be only predicated on view angle. Rather, as described above, the data segmentation is performed to derive images that are substantially free of artifacts. For example, the data inconsistency may be caused by cardiac motion in angiography, cardiac motion PET/SPECT/MRI cardiac function studies, respiratory motion in image-guided radiation therapy, inadvertent body motion in general purpose imaging tasks, contrast enhancement induced data inconstancy in time-resolved CT/MRI/PET/SPECT and cone beam CT angiography, beam hardening in x-ray CT and cone beam CT imaging due to the use of polychromatic x-ray sources and energy integration detectors, non-uniform noise distribution in projection data due to anisotropic human anatomy, metallic implant in CT and MRI studies, spectral inconsistencies in CT imaging, or combinations of these and other sources of artifacts. As such, commonalities of view angle or projections may not yield consistent data and, thus, a more detailed analysis such as described above and further detailed below is advantageous.

Also, in the case of other imaging modalities, the selection or segmenting of data may be performed based on criteria that is relevant to the imaging modality. For example, in MRI, different consistency constraints may be used for the center of k-space versus the periphery of k-space. As another non-limiting example, in the case of parallel MRI, each channel may serve as a basis to assemble segmented or localized datasets.

Referring to FIG. 4A and FIG. 5, at process block 410, the physically acquired data and the respective synthetic data are compared. As a non-limiting example, referring to FIG. 5, the physically acquired data X1-X12 and the corresponding synthetic data O1-O12 are subtracted to calculate a difference. As illustrated, this can be referred to as a "vertical analysis" because the physically acquired data X1-X12 and synthetic data O1-O12 pertain to the same underlying data, such as the same views or view angles of the subject 108, 210 (or common coil channels in MR).

As shown in FIG. 5, the vertical analysis yields values Δ1-Δ12 that then can be used at process block 412 to identify inconsistent data using a "horizontal analysis." In this non-limiting example, a "horizontal analysis" refers to comparing images or datasets that are adjacent to each other, either spatially and/or temporally or otherwise. That is, the data sets are from separately segmented or classified datasets. Thus, in the non-limiting example illustrated in FIG. 5, values Δ1-Δ12 are compared to identify that Δ8 represents horizontally inconsistent data with the remaining data.

At process block 414, compensation can be performed relative to the inconsistent data (in this example, Δ8). As a non-limiting example, data associated with Δ8 (i.e., X8 or O8) can be removed and the removed data replaced with data interpolated from X7 or O7 and/or X9 or O9. Also, the inconsistent data can be given a reduced weighting compared to the consistent data. Once any data inconsistencies have been identified and compensation performed, improved images can be reconstructed/delivered/displayed at process block 416.

Figure 4B:
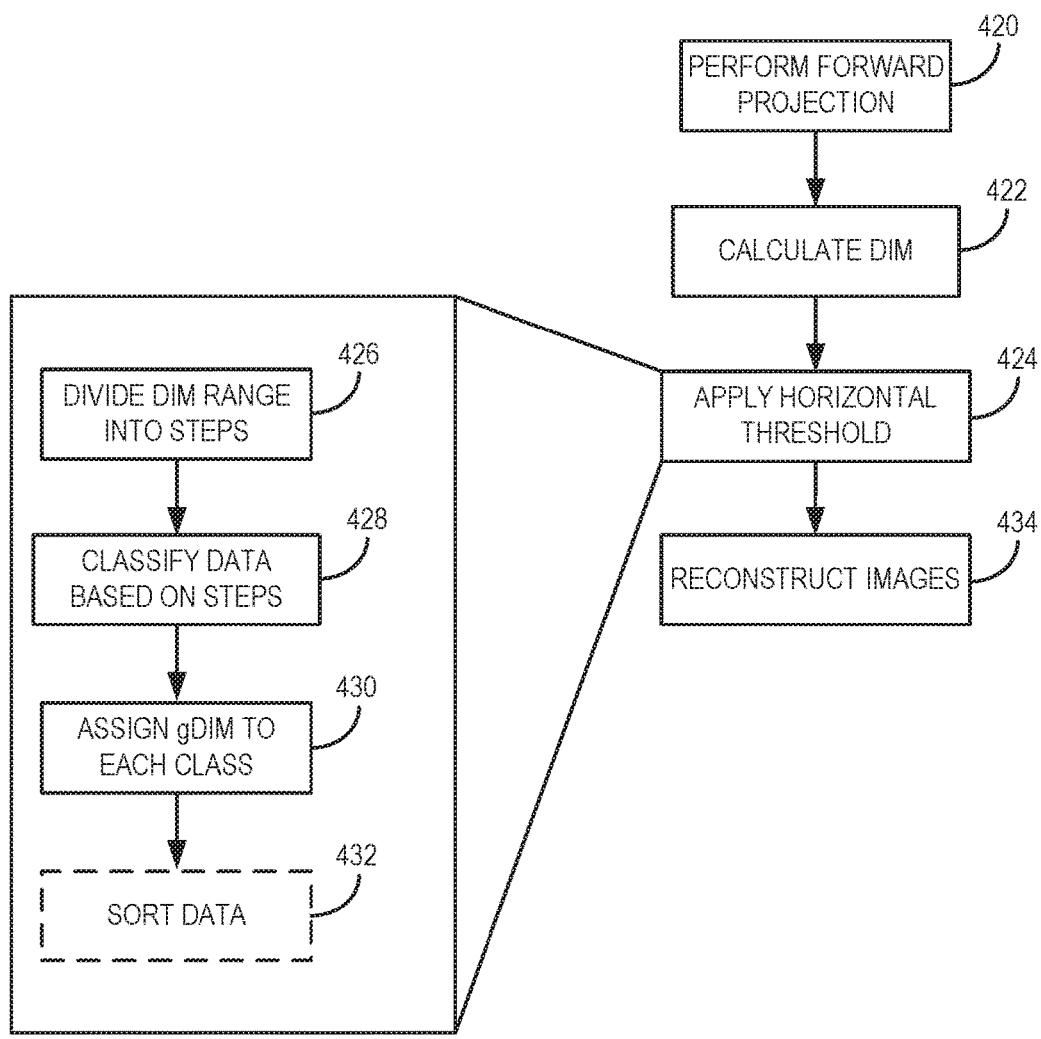
FIG. 4B is a flow char setting forth further non-limiting example steps of a method in accordance with the present disclosure.

Referring to FIG. 4B, one non-limiting example of a process spanning process blocks 408-416 will be described with respect to the non-limiting example of CT imaging. Specifically, at process bock 420, to generate synthetic image data in the context of CT imaging, a forward projection is performed at each corresponding view angle to generate a synthetic projection data set that has one-to-one, view-angle correspondence with the acquired projection data. This synthetic projection dataset of the prior image is a consistent dataset because it is based on the segmented data described above. This consistent dataset may be used as a reference to define data inconsistency level at each view angles for the acquired data. At process block 422, the normalized difference between the acquired projection dataset and the synthetic projection dataset is then calculated as follows to define a data inconsistency metric (DIM) for the data acquired at the corresponding view angle:

$$DIM(v) = \frac{\|Y(v) - Y_p(v)\|^2}{\|Y_p(v)\|_2} \in [0, 1]; \quad (4)$$

where v is the view angle index, $Y(v)$ is the vectorized projection data at the v-th view angle, while Y is the acquired projection data, and $Y_p$ is the synthetic forward projection of the prior image. A normalization factor, $\|Y_p(v)\|_2$, may be included. For example, if $D_1(v) = \|Y(v) - Y_p(v)\|_2$, a specific normalization may be given by $$D_2(v) = \frac{D_1(v)}{\max\{D_1(v)\}}$$

and DIM $(v) = D_2(v) - \min\{D_2(v)\}$. In this normalization, the range of DIM is DIM$\in [0, 1)$.

Using this non-limiting definition of DIM, when the calculated DIM is relatively constant across all the acquired data set (i.e., horizontal analysis), then the data set is a consistent data set. The fluctuations of DIM across individual view angles or physically acquired datasets reflects the level of inconsistency of a dataset. In some implementation, this determination may be achieved by applying a thresholding or other criteria at process block 424.

In one non-limiting example, a thresholding-based sorting or classification method can be applied with the DIM range divided into small steps at process block 426. In one non-limiting example, the small steps may create ten equally spaced sub-ranges: $[0, 0.1), [0.1, 0.2), \ldots, [0.9, 1.0]$. In this non-limiting example, the acquired data is classified into different consistency classes based on the steps at process block 428. For each consistency class, the following gross DIM (gDIM) can be defined at process block 430 as a single number to label the class:

$$gDIM(t) = \frac{1}{N_t} \sum_{v \in C_t} DIM(v); \quad (5)$$

where $C_t$ is a set of view angles of the t-th consistency class and $N_t$ is a normalization factor, which may be set to the number of views within the t-th class. After the projection data is sorted into different classes, the consistency level of data within each consistency class is improved. As described above, this process can be performed over the entire image field or it can be performed over one or more local regions of interest.

More generally, data within each consistency class is more consistent to each other and data within different consistency classes represent different information of the same image object. Hence, a data sorting scheme may also be used at process block 432 that is based on a definition of consistency class:

$$C_t = \{v \mid b_t \le DIM(v) < b_{t+1}\}; \quad (6)$$

$$b_t = \frac{DIM_{max}}{N} t, t = 0, 1, 2, \ldots N - 1. \quad (7)$$

Consistency classes can be said to satisfy the following conditions: $C_i \cap C_j = \emptyset, \forall i \ne j$; and $U_{t=0, 1, \ldots} C_t = \Theta$, where $\Theta$ is the set of all view angles or data. As will be described, the number of consistency classes N, can be optimized for use with a technique such as SMART-RECON. That is, in the case of CT imaging, there may be no common view angles among different classes. In such cases, the consistency classes are uniquely determined by N.

After this data processing is complete, image reconstruction can be performed at process block 434. As mentioned, reconstruction may be performed using the consistent data and/or with interpolated data, using the standard filtered backprojection (FBP) in CT or inverse FFT in MRI, or commercially available reconstruction methods in other modalities, such as PET and SPECT, provided that the selected consistent data satisfy the needed data sufficiency condition imposed by these known commercially available reconstruction methods. However, as will be described, it can be advantageous to utilize methods such as the SMART-RECON reconstruction technique to simultaneously reconstruct images for all consistent data classes.

Specifically, as described above, the above-described DIM and gDIM can be used to sort the data into N classes, with each class corresponding to set of data with high level of mutual consistency. The set of consistent data belonging to a given class can be jointly or disjointly distributed into independently prescribed projection or other ranges. This poses challenges to image reconstruction provided that the conventional image reconstruction strategy is used. Namely, in the case of projections in CT imaging, the image corresponds to a given view angle range is reconstructed individually.

Joint reconstruction of images of all consistency classes using SMART-RECON can be used to address this challenge for view angles sorted by the DIM or gDIM value at process block 432. That is, SMART-RECON can jointly reconstruct all image vectors from all consistency classes. Namely, by assigning an image vector to each consistency class, a total of N image vectors can be combined as columns of the image matrix X. These image columns can then be reconstructed by imposing a data fidelity condition for each consistency class and regularizing by the nuclear norm of the augmented image matrix $X_A=(\vec{X}_p|X)$, where $\vec{X}_p$ is a vectorized prior image.

That is, based on the definition of the consistency class in Eqn. (7), if the total number of consistency class is N, the data is divided into N classes in SMART-RECON. Each class corresponds to an image vector, so that the total of N image vectors can be arranged into an image matrix X. The SMART-RECON algorithm is then formulated to solve the following convex optimization problem:

$$\tilde{X} = \underset{X}{\operatorname{argmin}} \frac{1}{2} (\vec{y} - A\vec{X})^T D(\vec{y} - A\vec{X}) + \lambda \|X_A\|_*; \quad (8)$$

where $\vec{y}$ is the vecotrized projection data and $\vec{X}$ is the vectorized spatial-spectral image matrix, X. The diagonal matrix D has the inverse of the noise variance of the log-transformed data as its diagonal elements. $(\cdot)^T$ denotes the matrix transpose operation. The parameter $\lambda$ is introduced to control the balance between the data fidelity term and the regularizer strength. This prior image vector can be used to augment X to generate an augmented spatial-spectral matrix XA as follows:

$$X_A = (\vec{X}^p \mid X) := \begin{pmatrix} X_1^p & X_1^1 & X_1^2 & X_1^N \\ X_2^p & X_2^1 & X_2^2 & X_2^N \\ \cdots & \cdots & \cdots & \cdots \\ X_M^p & X_M^1 & X_M^2 & X_M^N \end{pmatrix}; \quad (9)$$

and the nuclear norm of this augmented image matrix can be used as the regularizer in the SMART-RECON algorithm as shown in Eqn. (8). Namely, the regularizer is given as:

$$\|X_A\|_* = \|U\Sigma V^T\|_* = \sum_r \sigma_r; \quad (10)$$

where $X_A = U\Sigma V^T$ is the singular value decomposition (SVD) of the matrix $X_A$. In this decomposition, U and V are two orthogonal matrices, and $\Sigma = \operatorname{diag}\{\sigma_r\}$ is a diagonal matrix with the singular values of $X_A$, $\sigma_r$ (r=1, 2, . . . ), as the diagonal entries. The details of numerical implementation of this construct of the SMART-RECON techniques are further described in U.S. Pat. No. 9,384,566 and co-pending U.S. application Ser. No. 15/211,448, both of which are incorporated herein by reference in their entirety.

Therefore, systems and methods are provided that yields improved images by creating locally consistent datasets. The systems and methods provided herein are applicable across imaging modality and does not depend on a specific data acquisition geometry or a specific data acquisition physics model.

Using the consistency-class based data sorting scheme, one can selectively use consistent data and the SMART-RECON algorithm to reconstruct images with mitigated spatial, temporal, and spectral-inconsistency caused image artifacts. The present systems and methods can be used with a single short-scan data acquisition and it does not require the explicit knowledge of tube potential, x-ray spectrum, or additional calibration procedures.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for reconstructing an image of a subject, the method including steps comprising:
    a) acquiring a reference dataset and reconstructing a prior image of the subject from the reference dataset;
    b) selecting at least a portion of the prior image that corresponds to a portion of the prior image of the subject that is free of artifacts;
    c) acquiring a medical imaging dataset of the subject;
    d) performing a first comparison of the medical imaging dataset and the reference dataset to create a data inconsistency metric;
    e) repeating steps b) though d) to create a plurality of data inconsistency metrics;
    f) performing a second comparison of the data inconsistency metrics to identify inconsistent data using the data inconsistency metrics;
    g) compensating for the inconsistent data identified in step f); and
    h) reconstructing an image of the subject with reduced artifacts compared to the prior image.

2. The method of claim 1 wherein step h) includes performing one of a filtered backprojection reconstruction, a SMART-RECON reconstruction, a Fourier transform-based reconstruction, or an iterative reconstruction.

3. The method of claim 1 further comprising acquiring, with a medical imaging system, the reference dataset or the medical imaging dataset.

4. The method of claim 3 wherein the medical imaging system includes one of a computed tomography system, a magnetic resonance imaging system, a positron emission tomography system, and a single photon emission computed tomography system.

5. The method of claim 1 wherein step g) includes at least one of removing or weighting the inconsistent data before step h).

6. The method of claim 1 wherein step g) includes dividing the plurality of data inconsistency metrics into classes based on predetermined data inconsistency metric steps.

7. The method of claim 1 wherein step h) includes initializing an image matrix having columns that each correspond to data in each of the classes and reconstructing a plurality of images of the subject by:
   i) minimizing a matrix rank of the image matrix;
   ii) constraining the rank minimization of step i) subject to a consistency condition that promotes a forward projection of each column in the image matrix to be consistent with a column in the image matrix.

8. The method of claim 6 further comprising assigning data in the medical imaging dataset to classes based on a global data inconsistency metric.

9. The method of claim 1 wherein step b) includes segmenting the prior image.

10. The method of claim 1 wherein step d) include performing a forward projection of the reference dataset using the at least the portion of the prior image to generate synthetic image data that is compared to the medical imaging dataset in the first comparison.

11. The method of claim 1 wherein step d) includes subtracting the synthetic image data and the medical imaging dataset.

12. A method for reconstructing an image of a subject, the method including steps comprising:
   a) generating synthetic image data using at least a portion of prior image data acquired from a subject;
   b) calculating a plurality of data inconsistency metrics by comparing the synthetic image data and medical imaging data;
   c) dividing the plurality of data inconsistency metrics into classes based on predetermined data inconsistency metric steps;
   d) initializing an image matrix having columns that each correspond to data in each of the classes;
   e) reconstructing a plurality of images of the subject by:
      i) minimizing a matrix rank of the image matrix; and
      ii) constraining the rank minimization of step e) i) subject to a consistency condition that promotes a forward projection of each column in the image matrix to be consistent with a column in the image matrix.

13. The method of claim 12 wherein step a) includes selecting the at least the portion of the prior image data to correspond to a portion of a prior image of the subject that is free of artifacts.

14. The method of claim 12 further comprising acquiring, with a medical imaging system, the prior image data.

15. The method of claim 14 wherein the medical imaging system includes one of a computed tomography system, a magnetic resonance imaging system, a positron emission tomography system, and a single photon emission computed tomography system.

16. The method of claim 12 wherein step b) includes performing a first comparison of the synthetic image data and the medical imaging data acquired from the subject to calculate the plurality of data inconsistency metrics.

17. The method of claim 16 further comprising performing a second comparison of the data inconsistency metrics to identify inconsistent data and compensating for the inconsistent data prior to step d).

18. A computed tomography (CT) system comprising:
   an x-ray source and associated detectors configured to acquire imaging data from a subject over a range of view angles;
   a computer system including a processor configured to:
      a) control the x-ray source and associated detectors to acquire imaging data from the subject;
      b) reconstruct the imaging data into a prior image of the subject;
      c) segment the prior image to create segmented imaging data that is substantially free of artifacts;
      d) generate synthetic image data using the segmented imaging data;
      e) calculate a plurality of data inconsistency metrics by comparing the synthetic image data and the segmented imaging data;
      f) divide the plurality of data inconsistency metrics into classes based on data inconsistency metric steps;
      g) initialize an image matrix having columns that each correspond to data in each of the classes;
      h) reconstruct a plurality of images of the subject by:
         i) minimizing a matrix rank of the image matrix; and
         ii) constraining the rank minimization of step h) i) subject to a consistency condition that promotes a forward projection of each column in the image matrix to be consistent with a column in the image matrix.

19. The CT system of claim 18 wherein step e) includes performing a first comparison of the synthetic image data and the imaging data to calculate the plurality of data inconsistency metrics.

20. The CT system of claim 19 further comprising performing a second comparison of the data inconsistency metrics to identify inconsistent data and compensating for the inconsistent data prior to step g).

21. A method for generating tomographic images comprising:
   a) acquiring a tomographic dataset of a subject;
   b) reconstructing the initial image from the tomographic dataset;
   c) generating a prior image of the subject that is free of artifacts from at least one of the tomographic dataset or initial image;
   d) generating a synthetic reference dataset from the prior image;
   e) performing a first comparison of the synthetic reference dataset and the tomographic dataset to create a plurality of data inconsistency metrics;
   f) performing a second comparison of data inconsistency level across the plurality of data inconsistency metrics;
   g) sorting the tomographic dataset into data consistency classes using the data inconsistency metrics;

h) selectively reconstructing a least one image from portions of the tomographic dataset determined to be consistent based on the data consistency classes; and i) selectively displaying the at least one image reconstructed at step h).

* * * * *